US00PP20531P2

(12) United States Plant Patent
Pan

(10) Patent No.: US PP20,531 P2
(45) Date of Patent: Dec. 8, 2009

(54) ***LANTANA* PLANT NAMED 'BANT REDA09'**

(50) Latin Name: *Lantana camara L.*
Varietal Denomination: Bant Reda09

(75) Inventor: Shifeng Pan, Hollister, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,127

(22) Filed: Nov. 6, 2008

(51) Int. Cl.
*A01H 5/00* (2006.01)

(52) U.S. Cl. ..... Plt./227

(58) Field of Classification Search ..... Plt./227
See application file for complete search history.

*Primary Examiner*—Annette H Para
(74) *Attorney, Agent, or Firm*—S. Matthew Edwards

(57) ABSTRACT

A new *Lantana* plant named 'Bant Reda09,' particularly distinguished by the red flower color, larger flowers, a relatively compact and mounding habit that is well branched, and has dark-green foliage.

1 Drawing Sheet

Latin name of the genus and species of the plant claimed: *Lantana camara L.*

Varietal denomination: 'Bant Reda09'.

BACKGROUND OF THE NEW PLANT

The present invention comprises a new *Lantana*, botanically known as *Lantana camara L.* and hereinafter referred to by the variety name 'Bant Reda09.'

'Bant Reda09' is a product of a planned breeding program. The new cultivar 'Bant Reda09' has red flower color, larger flowers, a relatively compact and mounding habit that is well branched, and has dark-green foliage.

'Bant Reda09' originated from a hybridization in a controlled breeding program in Gilroy, Calif. USA. The female parent was an unpatented hybrid seedling identified as '22-1' with fuschia color. '22-1' has lighter green foliage, is less compact, and is about 4–7 days later to flower than 'Bant Reda09.'

The male parent of 'Bant Reda09' was an unpatented hybrid seedling identified as '1–2' with a fuchsia/red color. 1–2 has a lighter flower color, is less branched, and less compact than 'Bant Reda09.'

'Bant Reda09' was selected as one flowering plant within the progeny of the stated cross in May 2005 in a controlled environment in Gilroy, Calif. USA. The pollination took place in July 2004 and the seed sowing in November 2004.

The first act of asexual reproduction of 'Bant Reda09' was accomplished when vegetative cuttings taken from the initial selection in May 2005 in a controlled environment in Gilroy, Calif. USA.

Horticultural examination of plants grown from cuttings of the plant initiated in May 2005 in Gilroy, California USA, and continuing thereafter, has demonstrated that the combination of characteristics as herein disclosed for 'Bant Reda09' are firmly fixed and are retained through successive generations of asexual reproduction.

'Bant Reda02' has not been observed under all possible environmental conditions. The phenotype may vary significantly with variations in environment such as temperature, light intensity and day length.

A Plant Breeder's Right for this cultivar was applied for in Canada on Dec. 24, 2007. 'Bant Reda09' has not been made publicly available more than one year prior to the filing of this application.

DESCRIPTION OF THE DRAWINGS

The accompanying photographic drawing shows typical flower and foliage characteristics of 'Bant Reda09' with colors being as true as possible with an illustration of this type. The photographic drawing shows a flowering potted plant of the new variety and a close-up of the flowers. The photographs were taken in Gilroy, Calif. USA. Both were grown in Gilroy, Calif. USA and were approximately 4 months old.

DETAILED BOTANICAL DESCRIPTION

The measurements were taken in Gilroy, Calif., in April 2008 on plants that were growing in 4 inch pots in a trial setting. Culture of these plants started in January 2008 in a greenhouse. The plants were approximately 4 months old.

Color Chart used: Royal Horticultural Society Colour Chart (R.H.S.) 2001

BRIEF SUMMARY OF INVENTION

The following observations, measurements, and comparisons describe plants grown outside in Gilroy, Calif. The following traits have been repeatedly observed and are determined to be basic characteristics of the new variety. The combination of these characteristics distinguishes this *Lantana* as a new and distinct variety.

TABLE 1

DIFFERENCES BETWEEN THE NEW VARIETY 'BANT REDA09' AND A SIMILAR VARIETY

| | 'Bant Reda09' | 'Bant Red09' (U.S. Plant Pat. No. 16,535) |
|---|---|---|
| Flower color | Deeper red | Lighter red |
| Plant habit | More compact | Less compact |
| Branching | Better branched | Less branched |

Plant:

*Form, growth and habit.*—Relatively compact and mounding habit, well branched; apical pinching enhances the number of branches and results in a tighter plant habit.

*Plant height.*—23–26 cm.

*Plant height* (*inflorescence included*).—27–30 cm.
*Plant width.*—39–44 cm.

Foliage:
*Type.*—Opposite.
*Immature, leaf color, upper surface.*—Closest to RHS 147A.
*Lower surface.*—Closest to RHS 147A.
*Mature, leaf color, upper surface.*—Darker than RHS 147A.
*Lower surface.*—Darker than RHS 147A.
*Length.*—6.3–7.5 cm.
*Width.*—4.4–5.6 cm.
*Shape.*—Attenuate.
*Apex shape.*—Acute.
*Margin.*—Serrate.
*Texture, upper surface.*—Hispid.
*Texture, lower surface.*—Hispid, mainly on the veins; glandular hairs
*Color of veins, upper surface.*—Both surfaces; RHS 144A basally, otherwise indistinct.
*Petioles color.*—RHS 144A.
*Petioles length.*—1.0–1.1 cm.
*Texture.*—Both surfaces, hispid; glandular hairs.

Stem:
*Color of stem.*—RHS 144A; no anthocyanins.
*Length of stem.*—22–27 cm.
*Diameter.*—0.4 cm.
*Length of internodes.*—2.5–3.5 cm.
*Texture.*—Hispid; glandular hairs.

Inflorescence:
*Type.*—Umbel like; flattened semi-sphere, the florets are sessile on an ovate receptacle.
*Blooming habit.*—Flowers continuously from spring through fall.
*Number of open flowers per inflorescence.*—20–30.
*Quantity of inflorescences per plant.*—20–25.
*Lastingness of individual blooms on the plant.*—About 4 weeks depending on temperatures.
*Fragrance.*—Slightly spicy.
*Umbel horizontal diameter.*—4.5–5.0 cm.
*Umbel vertical height.*—2.5–3.5 cm.
*Peduncle color.*—RHS 144A, no anthocyanins.
*Length of peduncle.*—2.7–3.2 cm.
*Peduncle diameter.*—0.2 cm.
*Texture.*—Hispid; glandular hairs.

Corolla:
*Floret form.*—Salver-shaped to shallow cup-shaped and zygomorphic, with a relatively long tube at the base.
*Length of floret.*—1.5 cm.
*Width of floret.*—1.0–1.2 cm.
*Immature, color of petals, upper surface.*—RHS 9A; sometimes with a margin of the slightest hue of RHS 44B to C.
*Lower surface.*—RHS 10B.
*Mature, color of petals, upper surface.*—RHS 23D overlaid with RHS N25B and finally changing from RHS 44A.
*Lower surface.*—Between RHS 53B and C.
*Petal length.*—0.6–0.7 cm.
*Petal diameter.*—0.7–0.8 cm.
*Apex.*—Mucronulate.
*Margin.*—Entire.
*Shape.*—Obovate.
*Degree of lobation.*—Moderate.
*Texture, upper surface.*—Papillose.
*Texture, lower surface.*—Slightly hirsute.
*Corolla tube, color, outer surface.*—RHS 53C with RHS 10C at base.
*Corolla tube, color, inner surface.*—RHS 10B.
*Corolla tube length.*—1.5 cm.
*Diameter* (*at opening*).—0.2 cm.
*Corolla tube texture, outer surface.*—Hispid.
*Corolla tube texture, inner surface.*—Hispid.

Bud (just before opening):
*Color.*—RHS 47A.
*Length.*—1.0–1.1 cm.
*Width.*—0.5 cm at the tip.
*Shape.*—Tubular.

Bract:
*Color.*—RHS 146C.
*Length.*—0.3–0.4 cm.
*Diameter.*—0.15–0.2 cm.
*Texture, upper surface.*—Glandular hairs.
*Texture, lower surface.*—Hirsute.

Calyx:
*Number of sepals.*—5, fused sepals forming a short tube around the base of each floret.
*Color of sepals.*—RHS 144B.
*Length of sepals.*—0.2–0.3 cm.
*Width of sepals.*—0.2 cm.
*Apex shape.*—Acute.
*Apex margins.*—Shallowly fringed.
*Texture, upper surface.*—Hirsute.
*Texture, lower surface.*—Glabrous.

Reproductive organs:
*Pistil.*—1.
*Length.*—0.4 cm.
*Style color.*—RHS 157A.
*Style length.*—0.3 cm.
*Stigma color.*—RHS 145C.
*Stamens.*—4.
*Color of filaments.*—RHS 10C.
*Length of filaments.*—0.5 cm.
*Anther color.*—RHS 13B.
*Length of anthers.*—0.1 cm.
*Pollen amount.*—Sparse.
*Color of pollen.*—RHS 10B.
*Fertility/seed set.*—This hybrid sets a sparse amount of seed and those seeds have not been observed for characteristics.

Disease/pest resistance: Disease resistance or susceptibility has not been observed on this hybrid.

What is claimed is:

1. A new and distinct variety of *Lantana* plant named 'Bant Reda09,' substantially as illustrated and described herein.

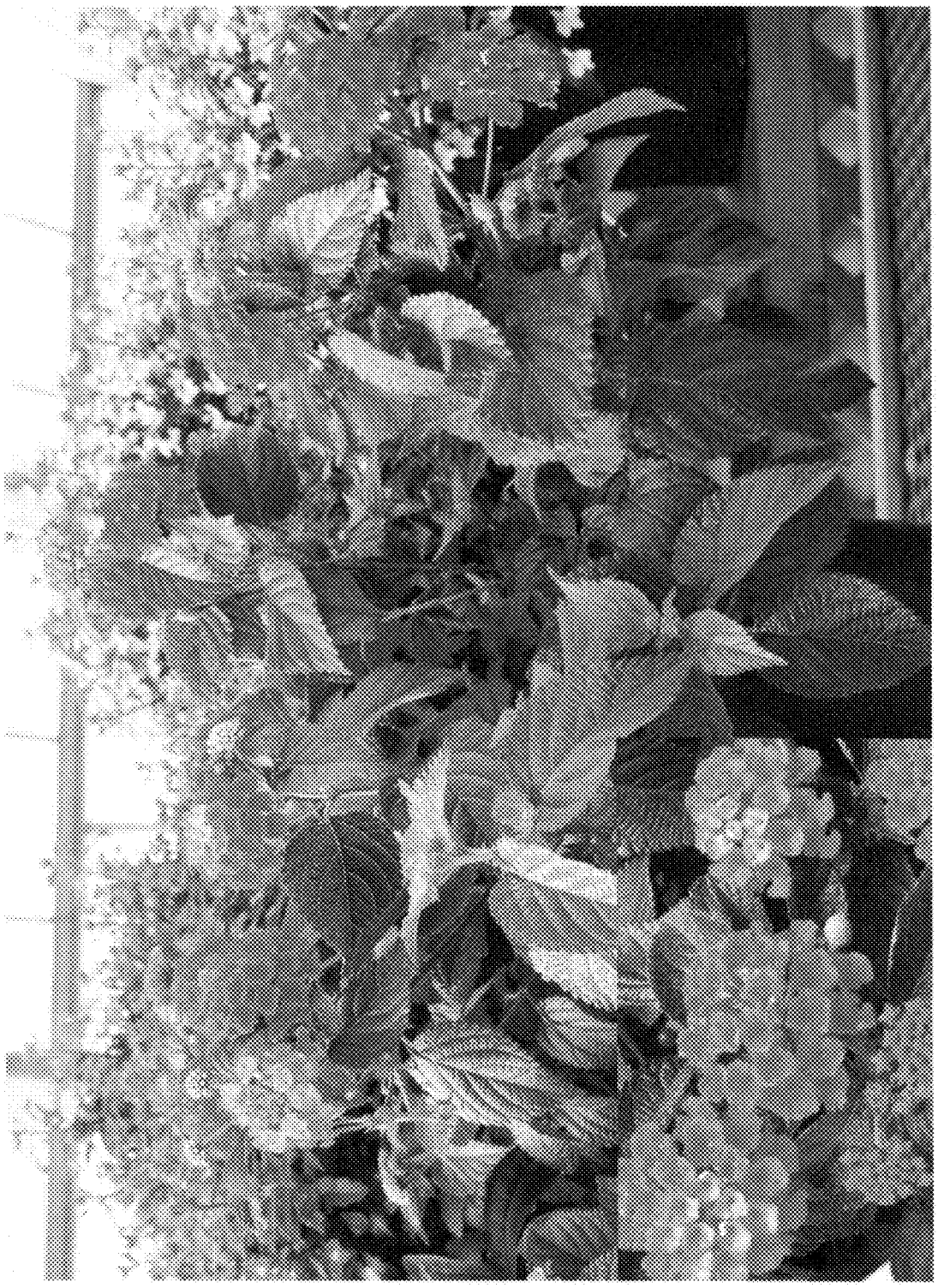

* * * * *